United States Patent [19]

Blanchard et al.

[11] Patent Number: 5,316,986
[45] Date of Patent: May 31, 1994

[54] TRIETHYNYLBORAZINES AND PRODUCTION OF BN CERAMICS THEREFROM

[75] Inventors: Christiane Blanchard, Le Breuil et Merleac; Evelyne Chassagneux, Millery; Gerard Mignani, Lyons; Michel Vaultier, Chateaugiron, all of France

[73] Assignee: Rhone-Poulenc Chimie, Courbevoie, France

[21] Appl. No.: 61,246

[22] Filed: May 17, 1993

[30] Foreign Application Priority Data

May 15, 1992 [FR] France .................. 92 05915

[51] Int. Cl.$^5$ .......................................... C04B 35/56
[52] U.S. Cl. .................................. 501/96; 528/7; 423/284
[58] Field of Search .............. 528/7; 501/96; 423/284, 423/353; 264/63, 65

[56] References Cited

U.S. PATENT DOCUMENTS

| | | | |
|---|---|---|---|
| 3,345,396 | 10/1967 | Horn | 528/7 |
| 3,382,279 | 5/1967 | Horn | 528/7 |
| 3,392,181 | 7/1968 | Horn | 528/7 |
| 4,714,599 | 12/1987 | Sato et al. | 423/290 |
| 4,971,779 | 11/1990 | Paine, Jr. et al. | 423/290 |
| 5,015,607 | 5/1991 | Ardaud et al. | 501/96 |
| 5,017,529 | 5/1991 | Blum et al. | 501/95 |
| 5,024,295 | 5/1991 | Paine, Jr. et al. | 501/96 |
| 5,071,935 | 12/1991 | Ardaud et al. | 528/5 |
| 5,096,861 | 3/1992 | Mignani et al. | 501/96 |
| 5,118,774 | 6/1992 | Mignani et al. | 528/7 |
| 5,162,558 | 11/1992 | Ardaud et al. | 556/402 |
| 5,202,399 | 4/1993 | Sneddoul et al. | 526/239 |

FOREIGN PATENT DOCUMENTS

0307260A1 3/1989 European Pat. Off. .

OTHER PUBLICATIONS

Chemical Abstracts, vol. 66, 1967, Columbus, Ohio; abstract No. 46478c, Nakagawa et al, p. 4415, & JP-A-41 021 778 (Shionogi & Co., Ltd.). .

Primary Examiner—Mark L. Bell
Assistant Examiner—A. Wright
Attorney, Agent, or Firm—Burns, Doane, Swecker & Mathis

[57] ABSTRACT

Novel boron/nitrogen compounds having the formula (1):

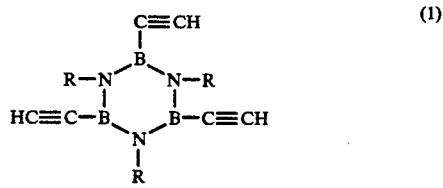

and the products of the at least partial reduction thereof, are converted into BN ceramic materials by thermally polymerizing same, whether or not in the presence of suitable polymerization catalyst, and then pyrolyzing the boron/nitrogen polymers thus obtained.

20 Claims, 1 Drawing Sheet

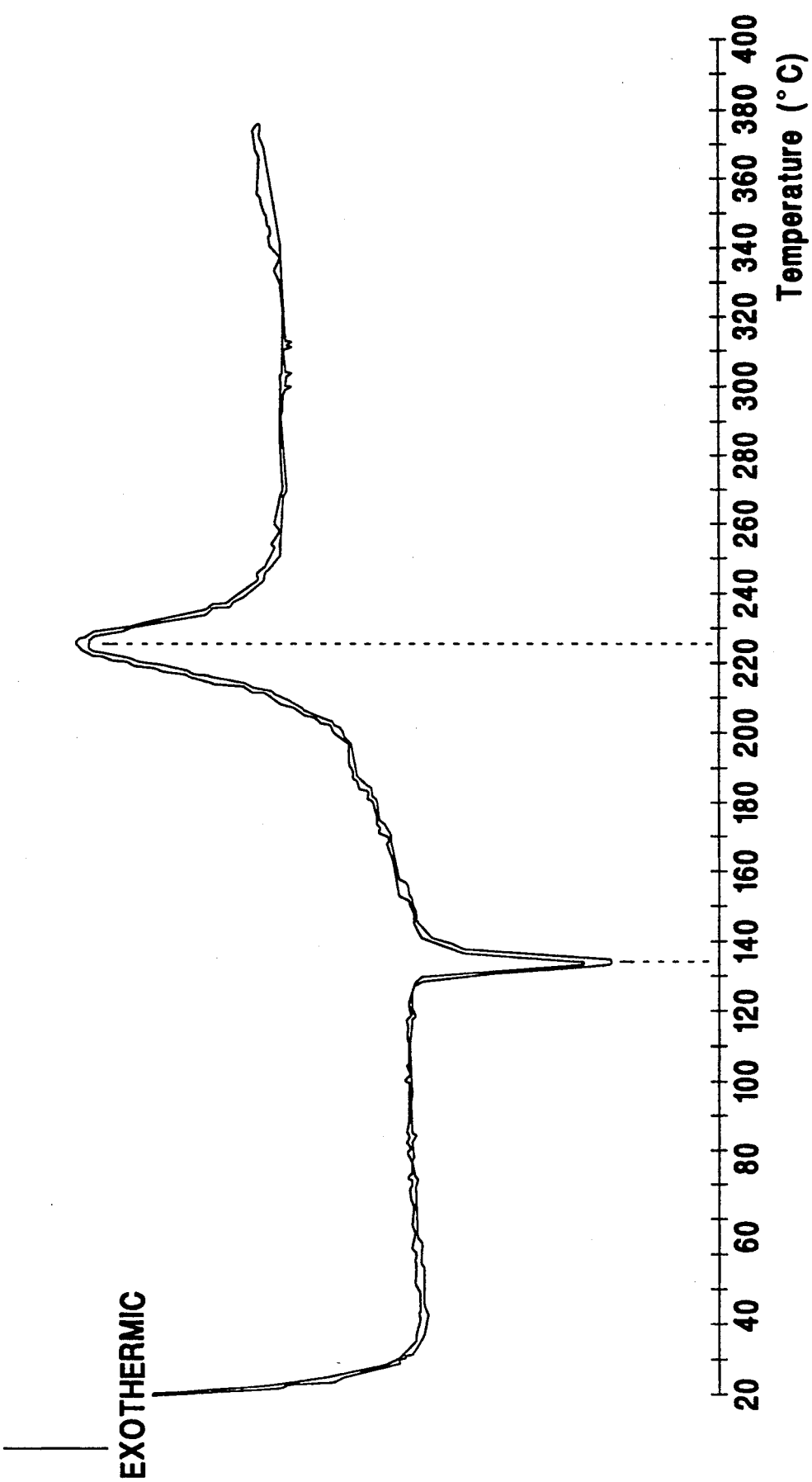

TRIETHYNYLBORAZINES AND PRODUCTION OF BN CERAMICS THEREFROM

BACKGROUND OF THE INVENTION

1. Field of the Invention

The present invention relates to novel borazine compounds and derivatives thereof, and to a process for the preparation of such novel borazines.

This invention also relates to the preparation of polymers based on boron and nitrogen from the subject novel borazine compounds thereof, as well as the production of ceramics based on boron nitride.

2. Description of the Prior Art

It is known to this art that boron nitride is an especially valuable material, in particular by reason of its stability at high temperatures, its resistance to thermal shock, its high chemical inertness and its very good heat-conductivity.

Various techniques for preparing boron nitride are presently known to the ceramic arts.

One such technique entails, for example, reacting a trihaloborane with ammonia in the gas phase. A powder of boron nitride is thus obtained which can be sintered to produce solid components.

However, the microporosity of the resulting components present disadvantages for certain applications.

More recently, boron nitride has been prepared by pyrolysis of organometal polymers based on boron and nitrogen.

The significance of this latter process is that it provides a wealth of options for shaping this type of product, in particular in the form of a coating or fibers.

It is thus known to this art to prepare polymers based on boron and nitrogen by aminolysis of compounds comprising boron, such as for example the trihaloboranes and the haloborazines. The polymers thus obtained are pyrolyzed to produce ceramics essentially comprising boron and nitrogen.

SUMMARY OF THE INVENTION

A major object of the present invention is the provision of novel compounds having the following formula (1):

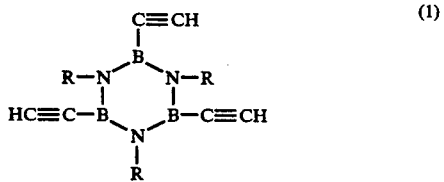

Another object of this invention is the conversion of such novel compounds, or derivatives thereof, into boron/nitrogen polymers and to the ultimate production of BN ceramics therefrom.

BRIEF DESCRIPTION OF THE DRAWING

FIG. 1 is a differential thermal analysis (DTA) of the solid product obtained in Example 1.

DETAILED DESCRIPTION OF PREFERRED EMBODIMENTS OF THE INVENTION

More particularly according to the present invention, the subject novel borazine compounds present a number of distinct advantages.

First, preparing polymers from these compounds does not require polymerization at very high temperatures.

Incipient polymerization of said novel compounds indeed, quite surprisingly, has been observed as soon as the temperature to which they were subjected was greater than their melting temperature.

Thus, because of their considerable reactivity, the use of such compounds for producing ceramics based on boron nitride is particularly easy whatever the process ultimately selected. It should, however, be noted that the advantage of these compounds is greater when they are employed in the form of coatings.

It therefore is no longer required, to produce a ceramic based on boron nitride in very high yields of pyrolysis (at least from 50% to 70%), to include an intermediate stage of polymer preparation, as was the case in most of the prior art techniques.

Indeed, it suffices to coat any suitable support, then to heat-treat such assembly, in the presence or in the absence of a catalyst, to polymerize, and, ultimately, to pyrolyze the polymer obtained.

The units >B—C≡CH constitute excellent cross-linking systems, in particular via a thermal, radical route or by use of transition metals.

Moreover, the compounds of formula (1) according to the invention are very easily converted, in good yields, into derivatives thereof wherein at least one of the triple carbon-carbon bonds is reduced to a double or a single carbon-carbon bond.

More particularly, the compounds of formula (1) can be converted into compounds in which the three triple bonds are reduced to carbon-carbon double bonds. Thus, trivinylborazines may be prepared via this technique and are advantageously used for the synthesis of boryl-containing homopolymers.

This latter type of compound also presents the advantage of being very reactive and, consequently, of polymerizing under gentle conditions, in the presence or absence of a catalyst. Moreover, the pyrolysis yields of the resulting polymers are on the same order of magnitude as those prepared by processing the compounds of formula (1).

An additional advantage of the derivatives prepared by reduction of the compounds according to the invention lies in that they are liquid at room temperature. It is therefore not necessary to solubilize them before use.

Thus, the present invention features novel compounds based on boron and nitrogen and having the formula (1):

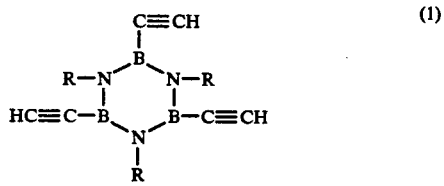

in which the radicals R, which may be identical or different, are each a hydrogen atom or an alkyl radical.

The Figure of Drawing illustrates a differential thermal analysis spectrum of a compound of formula (1) in which R is a hydrogen atom.

The present invention also features a process for preparing the subject novel compounds, comprising:

(a) reacting a monoanion of acetylene with a compound of formula (2):

$$(R_2N)_2B-X \qquad (2)$$

wherein X is a halogen and the radicals R, which may be identical or different, are each a $C_1-C_{10}$ alkyl, aryl, alkylaryl or arylalkyl radical; and (b) contacting the product thus obtained with a compound having at least one $NH_2$ functional group.

The present invention also features a technique for converting the compounds of formula (1), whereby the carbon-carbon triple bonds thereof are partially or totally reduced to double or optionally single carbon-carbon bonds.

Too, the present invention features a method for preparing polymers based on boron and nitrogen, comprising heat-treating the compounds of formula (1), or the products of reduction thereof, in the presence or absence of a catalyst of the anionic, cationic, radical type and/or based on transition metals.

Finally, the present invention also features a method for preparing ceramics based on boron nitride, 25, comprising pyrolyzing the polymers thus obtained in a reactive atmosphere such as $NH_3$, or a nonreactive atmosphere such as nitrogen or argon.

Thus, in a first respect, the present invention features a compound of formula (1) in which the radicals R, which may be identical or different, are each a hydrogen atom or an optionally substituted alkyl radical.

By "alkyl radical" are intended linear, branched or cyclic alkyl radicals.

More particularly, said alkyl radicals characteristically are $C_1-C_6$ alkyl radicals and are optionally substituted. Exemplary thereof are methyl, ethyl, propyl and its isomers, butyl and its isomers, pentyl and its isomers, cyclopentyl, hexyl and its isomers, and cyclohexyl radicals. The halogenated silyl derivatives of the above-mentioned radicals are also suitable according to the present invention. Preferably, the radicals R are each a hydrogen atom or an optionally substituted $C_1-C_3$ alkyl radical.

As indicated above, the compounds according to the invention exhibit a very good reactivity. Polymerized and crosslinked compounds can thus easily be prepared without the requirement for additional reactants.

moreover, in a second aspect of the invention, the carbon-carbon triple bonds of the compounds of formula (1) are reduced, totally or partially, into double and/or optionally single carbon-carbon bonds.

Preferably, the compounds obtained have at least one triple bond reduced to a carbon-carbon double bond and more particularly the three triple bonds are reduced to carbon-carbon double bonds.

Any technique for reducing triple bonds into double or single bonds is suitable according to the invention.

However, such reduction is preferably carried out by hydrogenation in the presence of a catalyst based on transition metals. More particularly, the metals are selected from among those of Group VIII of the Periodic Table of elements.

Hydrogenation may thus be carried out in the presence of a catalyst based on nickel, platinum, rhodium or palladium.

This reaction can be carried out in the presence of a homogeneous or heterogeneous catalyst.

If the reduction is carried out by heterogeneous catalysis, namely, in the presence of a catalyst which is insoluble in the reaction mixture, one of the metals indicative above, in its metallic state or in the form of the oxide thereof, can be used. Moreover, the metal or metals either may or may not be supported. Exemplary of suitable supports are carbon black or barium sulfate.

In the event that the reduction is carried out in homogeneous medium, the catalysts generally used are selected from among the organometallic complexes based on the aforesaid metals, which are soluble in the reaction mixture. Exemplary thereof are the Wilkinson catalysts, such as rhodium chlorotris(triphenylphosphine).

Usually, the hydrogenation is carried out in the presence of one or more solvents.

Solvents selected from among the linear or cyclic, saturated or aromatic $C_5-C_{12}$ hydrocarbons are suitable. Thus, exemplary thereof are pentane, hexane and its isomers, cyclohexane, toluene, benzene, and xylene and its isomers.

Solvents selected from among the esters and more particularly the esters produced by the esterification of acetic acid with a linear or cyclic, aliphatic or aromatic $C_1-C_{10}$ alcohol, such as, in particular, ethyl acetate and n-butyl acetate, are also suitable.

The hydrogenation is preferably carried out in an atmosphere, the hydrogen pressure or hydrogen partial pressure of which is controlled. Usually, a hydrogen partial pressure of approximately 1 atmosphere is used. Nonetheless carrying out this reaction utilizing a hydrogen pressure or a hydrogen partial pressure which is less or greater than that indicated above is also within the scope of the invention.

Moreover, the gas used may be pure hydrogen or hydrogen diluted in an inert gas such as the rare gases, such as argon or helium, or else in a gas such as nitrogen.

The temperature for carrying out the hydrogenation may vary over wide limits. Thus, the reaction may be carried out at temperatures ranging from 20° C. to 400° C. Preferably, the temperature ranges from room temperature to the reflux temperature of the solvent when the reduction is carried out in such a medium.

The process for preparing the compounds of formula (1) according to the invention comprises (a) reacting a monoanion of acetylene, having an ionic form of the formula $H-C\equiv C^- M^+$, with a second compound of formula (2):

$$(NR_2)_2B-X \qquad (2)$$

in which X is a halogen and the radicals R, which may be identical or different and either substituted or unsubstituted, are each hydrogen, an optionally substituted $C_1-C_{10}$ alkyl, alkenyl, alkynyl, aryl, alkylaryl or arylalkyl radical; and (b) then contacting the product thus obtained with a compound having at least one $NH_2$ functional group.

More particularly, the second compound is such that the halogen is chlorine or bromine.

Moreover, the radicals R, which may be identical or different, are preferably hydrogen or an optionally substituted $C_6-C_6$ alkyl, alkenyl, alkynyl, aryl, alkylaryl and/or arylalkyl radical.

In a preferred embodiment of the invention, the radicals R are each hydrogen or an optionally substituted $C_1-C_6$ alkyl radical.

Silicon substituents of these radicals are exemplary.

The compounds of formula (2) are known to this art and may be prepared by any known means.

Thus, W. Gerrard et al, *J. Chem. Soc.*, 381 (1957), describes, in particular, the reaction of a secondary amine (or its anion) with a haloborane, such as trichloroborane or tribromoborane, at a temperature ranging from 0° to 25° C. Thus, instead of haloborane, complexes of the type $BCl_3$, triethylamine; $BBr_3$, dimethylsulfide (DMS), may be used.

The compound of formula (2) is therefore contacted with a monoanion of acetylene having an ionic form of the formula $H-C\equiv C^- M^+$.

Preferably, $M^+$ is selected from among the elements of Group Ia of the Periodic Table of elements [P. Cadiot et al, *Bulletin de la SocieteChimique de France*, 12, 3846 (1966)] and the mixed organomagnesium compounds of the R-MGX type (X representing a halogen atom).

Preferably, $M^+$ is lithium, sodium, potassium or a mixed organomagnesium compound.

These compounds are prepared in conventional manner. Exemplary preparations of said monoanions include reactions of an alkyllithium compound, such as butyllithium, of sodium metal, or else of sodium hydride, with acetylene.

These reactions are generally carried out in the presence of an aprotic solvent.

Exemplary solvents suitable for the aforesaid reactions are linear or cyclic, saturated or unsaturated etheroxides, or linear or cyclic, saturated or unsaturated hydrocarbons.

It will be appreciated that these solvents should be dried prior to their use.

Ether, tetrahydrofuran, diglyme, hexane, cyclohexane, toluene, benzene, xylene and its isomers are solvents particularly suitable for preparing monoanions of acetylene.

Usually, preparation of these compounds is conducted at a temperature ranging from 0° C. to room temperature.

Moreover, while it is not required to perform the above reactions in a controlled atmosphere, it is preferable to conduct same in a neutral atmosphere such as nitrogen or argon.

The first step of the process according to the invention, i.e., the reaction of the monoanion of acetylene with the compound of formula (2), is typically carried out in a medium comprising a solvent.

The solvents indicated above in respect of the preparation of the monoanion are also suitable for carrying out said first step.

The temperature conditions are also comparable to those indicated above, namely, temperatures on the order of 0° C. to room temperature.

The order of introduction of the reactants is unimportant. However, it is preferable to introduce the compound of formula (2) into the reaction mixture comprising the monoanion. Advantageously, the monoanion of acetylene may be prepared, then the compound of formula (2) may be introduced immediately following completion of the reaction.

The second step of the process according to the invention entails contacting the product obtained from the first reaction with a compound having at least one $NH_2$ group.

Exemplary compounds of this type are ammonia, in particular, the primary amines comprising radicals which are saturated or unsaturated, substituted or unsubstituted.

Exemplary of the substituted amines are the silyl amines.

The diamines are also suitable according to the invention, such as, in particular, hydrazine, hydrazide, alkylhydrazines, and alkylhydrazides.

Ammonia and the primary amines are, however, preferably employed, in which the substituted or unsubstituted linear, branched or cyclic radical is a $C_1$-$C_{10}$ alkyl, alkenyl, alkynyl, aryl, alkylaryl or arylalkyl radical.

In a preferred embodiment of the invention, said compound is selected from among ammonia and the primary amines in which the substituted or unsubstituted linear, branched or cyclic radical is a $C_1$-$C_6$ alkyl, aryl, alkylaryl or arylalkyl radical.

Exemplary of such primary amines are methylamine, ethylamine, propylamine, isopropylamine, cyclopropylamine, butylamine, pentylamine and their isomers, and phenylamine.

Silylamines such as the triorganosilylamines, for example trimethylsilylamine, triethylsilylamine, or else the hydroorganosilylamines, such as hydrodimethylsilylamine, are also exemplary.

In a more preferred embodiment of the invention, ammonia or a primary amine comprising a $C_1$-$C_6$ alkyl radical is used.

The second step of the process according to the invention may be carried out neat, but is generally preferably conducted in the presence of a solvent. In this latter case, compounds of the saturated or unsaturated hydrocarbon type, and more particularly $C_5$-$C_{10}$ hydrocarbons may thus be used.

Pentane, hexane and their isomers, benzene, toluene, and xylene and its isomers, are exemplary solvents for carrying out this invention.

The temperature at which the second reaction of the invention is carried out is not critical. Temperatures ranging from room temperature to 3000C are typically employed.

Moreover, the reaction is preferably carried out in a controlled inert atmosphere such as nitrogen.

The present invention also features the preparation of ceramics based on boron nitride.

It is typically carried out in two steps.

Polymerization of the compound (1) and/or the product obtained from the reduction of the compound of formula (1) (hereinbelow designated the "reduced compound") is carried out in a first stage, and the polymer thus obtained is pyrolyzed in a second stage.

The first step is usually carried out at temperatures ranging from 50° C. to 200° C., in the presence or absence of a catalyst. Exemplary catalysts are of the anionic, cationic, or radical type and/or based on transition metals.

The lithium compounds, such as the alkyllithium compounds, and more particularly n-butyllithium and methyllithium, are exemplary catalysts of the anionic type.

The protonic acids or derivatives thereof, such as esters, are exemplary catalysts of the cationic type.

As such, the strong acids, such as perchloric acid and trifluoromethanesulfonic acid, as well as the derivatives thereof, such as the esters, are illustrative.

The polymerization reaction may also be carried out in the presence of Lewis acids or salts thereof.

As such, the metal salts of carboxylic acids, and more particularly naphthenates or octoates of the elements of the Groups VIIA, VIII, Ib to IVb of the Periodic Table of the elements [P. Cadiot et al, *Bulletin de la Societe Chimiaue de France*, 1981 (1966)] such as for example iron, zinc, manganese, lead, zirconium, are illustrative.

Similarly, the metal salts of inorganic acids are suitable for carrying out the invention, such as the sulfates, nitrates or chlorides of copper, silver, iron, cobalt, and nickel, in particular.

Finally, catalysts of the radical type may be used during this reaction, such as, for example, azobis-(isobutyro)nitrile.

The amount of catalyst used to carry out this step is usually less than 1.5% by weight based on the weight of compound (1) and/or of reduced compound.

In a very preferred embodiment of the invention, polymerization of the compound of formula (1) and/or of the reduced compound may be carried out without the requirement for a catalyst.

Indeed, it has surprisingly been determined that a simple heat treatment, in the absence of a catalyst, carried out at a temperature greater than the melting temperature of said compound (1) and/or of the reduced compound, is sufficient to effect polymerization of the latter.

The polymer obtained by processing the compound (1) and/or the reduced compound, may optionally be isolated, then shaped (coating, fiber, solid article).

After the polymerization reaction, pyrolysis of the polymer obtained from the first step is carried out. This step is usually carried out at a temperature ranging from 1,000° C. and 2,000° C., and more particularly at a temperature ranging from 1,200° C. to 1,800° C.

The pyrolysis can be carried out in an inert (or nonreactive) atmosphere, such as nitrogen or a rare gas such as helium or alternatively argon, or in a reactive atmosphere such as ammonia.

The ceramic thus produced is essentially based on boron, nitrogen and optionally carbon.

The various constituent amounts of these elements, and more particularly that of carbon, depend, in particular, on the atmosphere in which the polymer has been pyrolyzed.

Consequently, it is possible to regulate the carbon content in the final ceramic by varying the atmosphere in which the reaction is carried out and/or by varying the nature of R of the compound of formula (1).

In one particular embodiment of the invention, polymerization and pyrolysis are carried out without isolating in an intermediate stage the polymer obtained.

As indicated above, such an embodiment is of special interest in the event that ceramic coatings based on boron nitride are to be prepared on any suitable support.

Indeed, according to this particular embodiment, the aforesaid support is coated with the compound (1) and/or with the reduced compound, employed in the pure form or diluted in a solvent. The coating of the support is carried out by any means known to this art, such as impregnation, spraying, strip casting, brush casting or drop casting.

The material thus coated is then processed, in a single step, to polymerize, then pyrolyze the compound (1) and/or the reduced compound.

The temperature and atmosphere conditions during processing are comparable to those reported for processing with isolation of the polymer.

In order to further illustrate the present invention and the advantages thereof, the following specific examples are given, it being understood that same are intended only as illustrative and in nowise limitative.

EXAMPLE 1

Synthesis of

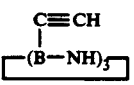

1. Synthesis of (iPr$_2$N)$_2$BCl 25.27 g (140.94 moles) of BCl$_3$/DMS complex were weighed into a 1-liter reactor, and dissolved in 500 ml of freshly distilled cyclohexane. The mixture was cooled to 0° C. and 79 ml of diisopropylamine were added while stirring vigorously; the mixture was permitted to react for 16 hours at 25° C. The precipitate formed was filtered under nitrogen; it was rinsed with dry cyclohexane. Bis(diisopropylamino)chloroborane was recovered by distillation (Eb$_{20}$=115°-120° C.). Yield of isolated product: 82%.

Mass spectrum: M$_{theoretical}$=246.2033 for C$_{12}$H$_{28}$N$_2$$^{10}$B$^{35}$Cl; M$_{obtained}$=246.2027.

RMN $^1$H (300 MHz), CDCl$_3$: 1.20 ppm/TMS - doublet (24 H, J=7 Hz), 3.46 ppm/TMS - heptuplet (4 H, J=7 Hz).

2. Synthesis of HC≡CB(iPr$_2$N)$_2$:

450 ml of dry THF were introduced into a 1-liter reactor under nitrogen, the contents were cooled to 0° C. and acetylene was bubbled through the THF for 30 minutes at 250° C. While continuing such bubbling of acetylene, 174 ml (278.48 mmol) of a solution of nBuLi (1.6 M) in hexane were slowly transferred therein. Bubbling of the acetylene was continued for 1 hour at 0° C.

An 0.75 molar equivalent of ClB(NiPr$_2$)$_2$ (51.5 g, 208.81 mmol) was then added at this temperature. The temperature was permitted to increase to 25° C., the solvent was evaporated under vacuum and distilled in a Vigreux column. 41.42 g of a crystallized compound were obtained. Yield in isolated product: 84%; melting point: 40° C.

RMN$^1$H (300 MHz), CDCl$_3$: 1.23 ppm/TMS - doublet (24 H, J=7 Hz), 2.76 ppm/TMS - singlet (1 H), 3.41 ppm/TMS - heptuplet (4 H, J=7 Hz ).

IR (nujol, NaCl): 2060 cm$^{-1}$ (—C≡C—); 3290 cm$^{-1}$ (≡C—H).

Analysis: C$_{14}$H$_{29}$N$_2$$^{10}$B calculated: % C=71.18, % H=12.28, % N=11.85, found: % C=71.44, % H=11.97, % N=11.72, 3. Synthesis of:

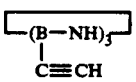

6.71 g of HC≡CB(iPr$_2$N)$_2$ and 40 ml of dry toluene were introduced into a three-necked flask under nitrogen. Ammonia was then added and the medium was heated to 105° C. in order to distil diisopropylamine, the flow rate of ammonia was maintained for 6 hours, 30 min at this temperature. Ammonia was stopped when the amine ceased to distil. The toluene was the removed under vacuum and the residue was sublimed under 0.05 mm of Hg, at 103° C. A crystallized white solid was recovered with a yield of 75.7% and a melting point of 142° C. (see the differential thermal analysis of the Figure of Drawing).

IR (KBr): 1484 cm$^{-1}$ (BN); 2075 cm$^{-1}$ (C≡C); 3266 cm$^{-1}$ (≡C-H); 3414 cm$^{-1}$ (NH).

RMN$^1$H (300 MHz), CDCl$_3$: 2.60 ppm/TMS—singlet (1 H, ≡C-H), 5 5.54 ppm/TMS—singlet (3 H, = NH), RMN$^{13}$C (360 MHz), CDCl$_3$: 75 ppm (>B—C≡C—H), 93.5 ppm (>B—C≡C—H), Mass spectrum: m/e = 153.

Converting this compound into a ceramic at 1,000° C. under ammonia produced a white solid which was then pyrolyzed at 2,000° C. under nitrogen. Infrared and X-ray analyses evidenced the formation of boron nitride (BN).

EXAMPLE 2

1 molar equivalent of (pir$_2$N)$_2$BLi by weight at 75° C. was reacted with a large excess of ammonia to produce a solid which was infusible and soluble in dimethylacetamide. The chromatography spectrum by gel permeation of this compound evidenced the existence of numerous oligomers comprising 2 and/or 3 monomers, or more.

The infrared spectrum showed the following characteristic bands:

3430 cm$^{-1}$ (NH), 3050 cm$^{-1}$ (CH), 1616 cm$^{-1}$ (C=C), 1011 cm$^{-1}$ (CH), 949 cm$^{-1}$ (CH$_2$), 1480 cm$^{-1}$ (BN) ("stetches"), 740 cm$^{-1}$ (BN) (deformation), 2875 cm$^{-1}$-1 (CH$_2$).

Converting this resin into a ceramic at 1,000° C. under nitrogen produced, in a yield by weight of 62%, a black solid which was then pyrolyzed at 2,000° C. under nitrogen. The yield by weight of this pyrolysis was 92%.

The X-ray analyses of the solid evidenced the formation of BN.

The density was 1.71.

The elemental analyses corresponded to a molar composition of the type:

BN$_{1.2}$C$_{0.6}$

In this ceramic, the percentage of oxygen was 2.3% (by weight), that of hydrogen was 0.5% (by weight).

EXAMPLE 3

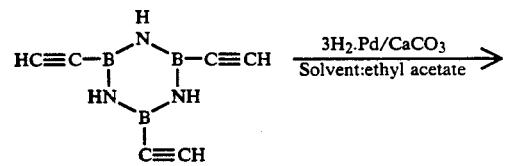

152 mg (1mmole) of triethynylborazine obtained according to the procedure of Example 1 were weighed into a 10 ml reactor and dissolved in 2.5 ml of dry ethyl acetate. 10% by weight of Pd/CaCO$_3$ catalyst, i.e., 15 mg, and approximately 1 mg of poison for Lindlar catalyst [Fluka, reference 62150, [2,2'-(ethylenedithio) diethanol]] were added.

The reactor was connected to the hydrogenation system (PARR apparatus) and, after purging several times in succession with hydrogen, hydrogenation was begun. When 3 equivalents of hydrogen (i.e., 67 ml) had been absorbed, the hydrogenation was stopped.

The suspension was filtered over cellite, the solvents were removed under vacuum to yield an oil which was purified in a bulb tube (Bp$_{0.05}$=48°-50° C.). 135 mg of a mixture of molar ratio of 87/13 of trivinylborazine and triethylborazine were obtained.

Analysis of trivinylborazine

RMN$^1$H (300 MHz) CDCl$_3$, δppm/TMS: 5.07 (s broad, 3H); 5.76-5.85 (m, 6H); 5.91-6.09 (m, 3H).

RMN$^{13}$C (75.5 MHz) CDCl$_3$, δppm/TMS: 130.4; 136.2. Mass spectrum: calculated mass for C$_6$H$_{12}^{11}$B$_3$N$_3$: M theoretical = 159.1310; M obtained = 159.1322.

After having isolated trivinylborazine, a number of trivinylborazine polymerization tests were carried out. The results obtained are reported in the following Table:

TABLE

| Initiator | Mode of operation | Results |
|---|---|---|
| Triflic acid (TA) | 1 g of trivinylborazine 0.9% (by weight) (TA) 3 h, 60° C. then 2 h, 20° C. | Gel: infusible, insoluble<br>IR analysis: little of B  |
| AIBN | 0.9 g of trivinylborazine 2.1% (by weight) of AIBN 1 h, 55° C. | Gel: infusible, insoluble<br>IR analysis: little of B |
| AIBN | 4.57 g of trivinylborazine 0.99% (by weight) of AIBN 1 h, 40 min at 50° C. | Loss of mass: 2.3%<br>Gel: infusible, insoluble<br>IR analysis: little of B |
| nBuLi | 1.3 g of trivinylborazine 1.17% (by weight) of nBuLi 1 h, 30 min at 50° C., then 3 h at 120° C. | Gel: infusible, insoluble<br>IR analysis: little of B |

These results indicate that it is very easy to homopolymerize trivinylborazine by the cationic, radical or anionic route.

Pyrolysis of the crosslinked polymers obtained below under NH$_3$ or nitrogen provided, in yields of 50% to 70%, ceramics of BCN type. Depending on the nature of the pyrolysis atmosphere, it is possible to adjust the final % of C.

EXAMPLE 4

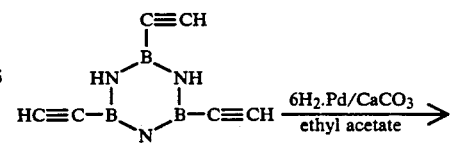

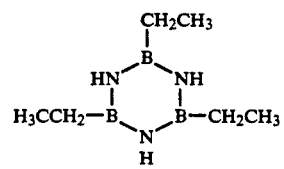

181 mg (1.18 mmol) of triethynylborazine obtained according to the procedure of Example 1 were weighed

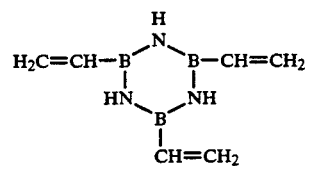

into a 10 ml reactor and dissolved in 2.5 ml of dry ethyl acetate; 10% by weight of Pd/CaCO$_3$ (Lindlar catalyst) was added. This reactor was connected to the hydrogenation system (PARR apparatus). After purging the apparatus several times in succession with hydrogen, hydrogenation was initiated.

After absorbing 160 ml of hydrogen (6 equivalents), the suspension was filtered over cellite, the solvents were evaporated, and a clear oil was obtained.

After purifying by means of a bulb tube (Bp$_{0.05}$=60° C.-62° C.), 130 mg of triethylborazine were obtained. RMN $^1$H (300 MHz) CDCl$_3$, δ ppm/TMS=0.71-0.81 (m, 3H); 0.82-0.96 (m, 9H); 4.66 (s, 3H). RMN$^{13}$C (75.5 MHz) CDCl$_3$, δ ppm/TMS; 8.76; 9.51.

Mass spectrum: calculated mass for C$_6$H$_{18}$$^{11}$B$_3$N$_3$=M theoretical=165.1779; M obtained=165.1790.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound having the formula (1):

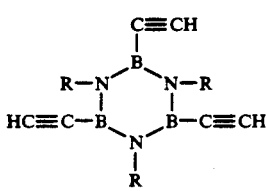
(1)

wherein the radicals R, which may be identical or different, are each a hydrogen atom, an alkyl radical or a substituted alkyl radical.

2. The compound as defined by claim 1, wherein the radicals R, which may be identical or different, are each a hydrogen atom or a C$_1$-C$_6$ alkyl radical.

3. The compound as defined by claim 2, wherein the radicals R, which may be identical or different, are each a hydrogen atom or a C$_1$-C$_3$ alkyl radical.

4. The compound as defined by claim 1,. wherein the radicals R, which may be identical or different, are each a hydrogen atom, an alkyl radical or a halosilylated alkyl radical.

5. The compound as defined by claim 1, wherein the radicals R are each a hydrogen atom.

6. A compound having the formula:

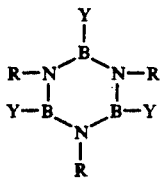

wherein the radicals Y are ethyl, vinyl or ethynyl radicals, at least one of which being an ethynyl radical, and the radicals R, which may be identical or different, are each a hydrogen atom or an optionally substituted alkyl radical.

7. A process for the preparation of the compound as defined by claim 1, comprising (a) reacting an acetylene monoanion of the formula H—C≡$^-$M$^+$, wherein M$^+$ is an element of Group Ia of the Periodic Table, or a mixed organomagnesium compound; with a compound having the formula (2):

$$(R_2N)_2B-X \qquad (2)$$

wherein X is a halogen atom and the radicals R, which may be identical or different, are each a hydrogen atom or an optionally substituted C$_1$-C$_{10}$ alkyl, aryl, alkenyl, alkynyl, alkylaryl or arylalkyl radical, and (b) contacting the product of reaction thus obtained with a nitrogen compound having at least one NH$_2$ group.

8. The process as defined by claim 7, wherein said compound having the formula (2), X is chlorine or bromine.

9. The process as defined by claim 7, wherein said compound having the formula (2), the radicals R, which may be identical or different, are each a hydrogen atom or a C$_1$-C$_6$ alkyl, alkenyl, alkynyl, aryl, alkylaryl or arylalkyl radical.

10. The process as defined by claim 7, wherein said acetylene monoanion, M$^+$ is selected from the group consisting of lithium, sodium, and potassium.

11. The process as defined by claim 7, wherein said nitrogen compound is ammonia or a primary amine.

12. The process as defined by claim 7, further comprising reducing at least one of the carbon-carbon triple bonds of said compound of formula (1) into carbon-carbon double bonds and/or optionally into carbon-carbon single bonds.

13. The process as defined by claim 12, comprising reducing at least one of the carbon-carbon triple bonds of said compound of formula (1) into a carbon-carbon double bond.

14. The process as defined by claim 12, comprising conducting such reduction by hydrogenation in the presence of a catalytically effective amount of a homogeneous or heterogeneous catalyst.

15. The process as defined by claim 14, said catalyst comprising a metal of Group VIII of the Periodic Table.

16. A process for the preparation of a boron and nitrogen containing, comprising thermally treating a compound as defined by claim 1, or a product of the at least partial reduction thereof.

17. The process as defined by claim 16, carried out in the presence of a catalytically effective amount of an anionic, cationic or radical polymerization catalyst, or a transition metal polymerization catalyst.

18. The process as defined by claim 17, said polymerization catalyst comprising azobis(isobutyro)nitrile, trifluoroacetic acid, perchloric acid or an organolithium compound.

19. A process for the production of a boron nitride containing ceramic material, comprising pyrolyzing the polymer product of the process as defined by claim 16.

20. A process for the production of a boron and nitrogen containing ceramic material, comprising coating a compound as defined by claim 1, or a product of the at least partial reduction thereof, onto a shaped substrate, next thermally converting said compound into a boron and nitrogen containing polymer, and thence pyrolyzing said polymer.

* * * * *